United States Patent [19]

Wu

[11] Patent Number: 5,276,242

[45] Date of Patent: Jan. 4, 1994

[54] ALKYLATION PROCESS

[75] Inventor: An-hsiang Wu, Bartlesville, Okla.

[73] Assignee: Phillips Petroleum Company, Bartlesville, Okla.

[21] Appl. No.: 49,926

[22] Filed: Apr. 20, 1993

Related U.S. Application Data

[63] Continuation-in-part of Ser. No. 936,152, Aug. 26, 1992, abandoned.

[51] Int. Cl.$^5$ .............................................. C07C 2/58
[52] U.S. Cl. .................................. 585/709; 585/725; 585/728; 585/730; 585/731
[58] Field of Search ............... 585/709, 713, 725, 727, 585/728, 730, 731

[56] References Cited

U.S. PATENT DOCUMENTS

| | | | |
|---|---|---|---|
| 2,820,074 | 1/1958 | Pines | 260/683.49 |
| 3,248,343 | 4/1966 | Kelly et al. | 252/442 |
| 3,271,299 | 9/1966 | Kearby | 208/114 |
| 3,324,750 | 9/1967 | Kearby | 252/437 |
| 3,328,272 | 3/1966 | Nixon | 260/683.65 |
| 3,420,909 | 1/1969 | Schmerling | 260/671 |
| 3,502,735 | 3/1970 | Copelin | 260/658 |
| 3,631,211 | 12/1971 | Schmerling | 260/668 C |
| 3,655,797 | 4/1972 | Schmerling | 260/671 |
| 3,846,503 | 11/1974 | Schmerling et al. | 260/666 P |
| 3,976,714 | 8/1976 | Rodewald | 260/683.47 |
| 4,929,800 | 5/1990 | Drago et al. | 585/744 |

FOREIGN PATENT DOCUMENTS

| | | |
|---|---|---|
| 1245853 | 10/1987 | Japan . |
| 1-245853 | 10/1989 | Japan ................. 785/730 |

OTHER PUBLICATIONS

N. Kitajima, "Two Component Friedel-Crafts Catalysts", Materials Chemistry and Physics 17(1987), pp. 31–48.

N. Kitajima et al., "Cu(AlCl$_4$)$_2$ as a Catalyst for the Isomerization of Pentane at Room Temperature", Journal of Molecular Catalysis 10 (1981), pp. 121–122.

Y. Ono et al., "Isomerization of Pentane with AlCl$_3$–CuSO$_4$ Mixtures", Journal of Catalysis 64 (1980), pp. 13–17.

Y. Ono et al., "Isomerization of Pentane with Aluminum Chloride (Gallium Chloride)–Cupric Salt Complexes", Proceedings 7th Internat. Congress Catalys., Tokyo, 1980, pp. 1006–1017.

Primary Examiner—Asok Pal
Assistant Examiner—P. Achutamurthy
Attorney, Agent, or Firm—K. K. Brandes

[57] ABSTRACT

In one embodiment of this invention, a process for alkylating $C_3$–$C_6$ alkanes (paraffins) with $C_3$–$C_6$ alkenes (monoolefins) employs a catalyst composition which has been prepared by heating a mixture consisting essentially of aluminum chloride, at least one metal sulfate ($CuSO_4$, $FeSO_4$, $NiSO_4$, $MgSO_4$, $CaSO_4$ or combinations thereof), at least one inorganic refractory support material (alumina, silica, silica-alumina, aluminum phosphate, aluminum phosphate/oxide or combinations thereof), and at least one chlorinated hydrocarbon (preferably carbon tetrachloride). In another embodiment of this invention, a process for alkylating $C_3$–$C_6$ alkanes with $C_3$–$C_6$ alkenes employs a catalyst which has been prepared by heating a mixture consisting essentially of aluminum chloride, aluminum phosphate, silica, and at least one chlorinated hydrocarbon (preferably carbon tetrachloride).

20 Claims, No Drawings

ALKYLATION PROCESS

This is a continuation-in-part of U.S. patent application Ser. No. 936,152, filed Aug. 26, 1992, abandoned.

This invention relates to the alkylation of alkanes (paraffins) with alkenes (monoolefins), in the presence of novel solid catalysts comprising aluminum chloride.

The use of catalysts which contain aluminum chloride for the alkylation of hydrocarbons is known. The present invention is directed to modifying these alkylation catalysts so as to enhance their activity.

SUMMARY OF THE INVENTION

It is an object of this invention to alkylate alkanes with alkenes in the presence of novel solid catalysts comprising aluminum chloride. Other objects and advantages will be apparent from the detailed description of the appended claims.

In accordance with this invention, a process for alkylating alkanes comprises the step of contacting at least one feed alkane (i.e., at least one straight-chain alkane or at least one branched alkane or a mixture thereof) containing about 3–6 carbon atoms per molecule with at least one alkene (i.e., at least one straight chain alkene or at least one branched alkene or a mixture thereof) containing about 3–6 carbon atoms per molecule with at least one solid catalyst composition at effective alkylation conditions, so as to form an alkylate comprising at least one product alkane which contains a greater number of carbon atoms per molecule (preferably 3–6 more) than said at least one feed alkane; wherein said solid catalyst composition has been prepared by a preparation method comprising (preferably consisting essentially of) the preparation steps of:

(1) heating for a period of at least 1 hour, at a temperature in the range of about 40° C. to about 90° C., in the substantial absence of water, a mixture comprising (preferably consisting essentially of): (a) aluminum chloride, (b) at least one metal sulfate selected from the group consisting of copper(II) sulfate, nickel(II) sulfate, cobalt(II) sulfate, iron(II) sulfate, magnesium sulfate and calcium sulfate, (c) at least one solid inorganic refractory material having a BET/$N_2$ surface area of at least about 50 $m^2/g$ selected from the group consisting of alumina, silica, silica-alumina, aluminum phosphate and aluminum phosphate/oxide, and (d) at least one chlorinated hydrocarbon having a normal boiling point (i.e., a boiling point at a pressure of about 1 atm.) of about 40°–90° C.; wherein the molar ratio of aluminum chloride to said at least one metal sulfate is at least about 2:1; and (2) separating the solid component of the reaction mixture formed in step (1) from the at least one chlorinated hydrocarbon under a dry gas atmosphere.

In a preferred embodiment, agent (d) is carbon tetrachloride. Preferably, the heating time of preparation step (1) is about 5–30 hours. In another preferred embodiment, preparation step (2) is carried out in two substeps: filtering the reaction mixture formed in step (1) so as to recover the solid component therefrom, and subsequently drying the recovered solid material (i.e., substantially removing volatile substances, in particular the at least one chlorinated hydrocarbon, therefrom).

Also in accordance with this invention, a process for alkylating alkanes comprises the step of contacting at least one feed alkane (i.e., at least one straight-chain alkane or at least one branched alkane or a mixture thereof) containing about 3–6 carbon atoms per molecule with at least one alkene (i.e., at least one straight chain alkene or at least one branched alkene or a mixture thereof) containing about 3–6 carbon atoms per molecule with at least one solid catalyst composition at effective alkylation conditions, so as to form an alkylate comprising at least one product alkane which contains a greater number of carbon atoms per molecule (preferably about 3–6 more) than said at least one feed alkane; wherein said solid catalyst composition has been prepared by a preparation method comprising (preferably consisting essentially of) the preparation steps of:

(A) heating for a period of at least 1 hour, at a temperature in the range of about 40° C. to about 90° C., in the substantial absence of water, a mixture comprising (preferably consisting essentially of): (i) aluminum chloride, (ii) aluminum phosphate, (iii) silica having a BET/$N_2$ surface area of at least about 50 $m^2/g$, and (iv) at least one chlorinated hydrocarbon having a normal boiling point (i.e., a boiling point at a pressure of about 1 atm.) of about 40°–90° C.; and (B) separating the solid component of the reaction mixture formed in step (A) from the at least one chlorinated hydrocarbon mixture under a dry gas atmosphere.

In a preferred embodiment, agent (iv) is carbon tetrachloride. Preferably, the heating time of preparation step (A) is about 5–30 hours. In another preferred embodiment, preparation step (B) is carried out in two substeps: filtering the reaction mixture formed in step (A) so as to recover the solid material therefrom, and subsequently drying (i.e., substantially removing volatile substances from) the recovered solid.

DETAILED DESCRIPTION OF THE INVENTION

The term "at least one", whenever it is used herein, means: one substance or a mixture of two or more substances selected from a specific group of substances.

Step (1) of the first method for preparing catalysts employed in the alkylation process of this invention can be carried out in any suitable manner in any suitable vessel. Generally, substantially dry agents (a), (b), (c) and (d), which are defined above, are thoroughly mixed under a dry inert gas atmosphere ($N_2$, He, Ar and the like), and then heated under a dry inert gas atmosphere at a temperature of about 40°–90° C., preferably about 70°–80° C., for a time period of about 4 to about 125 hours, preferably about 10–30 hours, more preferably 15–25 hours. It is preferred to carry out step (1) with agitation, either mechanically (e.g., by means of a stirrer) or ultrasonically.

The molar ratio of agent (a), i.e., $AlCl_3$, to agent (b), i.e., the at least one metal sulfate (listed above), preferably $CuSO_4$, should be at least about 2:1, preferably is about 2:1 to about 10:1, and more preferably is about 5:1 to about 6:1. Generally, the ratio of the combined weight of agents (a) and (b) to the weight of agent (c), i.e., the at least one solid inorganic refractory material (listed above), is in the range of about 0.5:1 to about 5:1, preferably about 1:1 to about 2:1. These inorganic refractory materials are either commercially available or can be prepared by known methods. The surface area of agent (c) should be at least about 50 $m^2/g$, preferably about 100–400 $m^2/g$, as determined by the well known method of Brunauer, Emmett and Teller (BET method) employing nitrogen. Preferred refractory support materials are those consisting essentially of alumina, silica, silica-aluminas having a silica:alumina weight ratio of about 1:5 to about 1.5:1 (more preferably about 1:4 to about 1:1; generally having been prepared by coprecipitation of hydrated silica and hydrated alumina, followed by drying and calcining), aluminum phosphates (generally having an atomic Al:P ratio of about 1:1 to about 2:1), and aluminum phosphate/oxides (having an atomic Al:P ratio of about 0.6:1 to about 10:1; generally having been prepared by coprecipitation of aluminum phosphate and hydrated alumina, followed by drying and calcining).

Agent (d) is a chlorinated hydrocarbon or a mixture of two or more chlorinated hydrocarbons having a normal boiling point in the range of about 40°–90° C., preferably about 70°–80° C. Non-limiting examples of agent (d) include dichloromethane, chloroform (trichloromethane), carbon tetrachloride, 1,1-dichloroethane, 1,2-dichloroethane, 1,1,1-trichloroethane, 1,1-dichloropropane, 2,2-dichloropropane, 1-chlorobutane, 2-chloro-2-methylbutane, and mixtures thereof. The preferred agent (d) is carbon tetrachloride. Generally, the ratio of the weight of agent (d) to the combined weight of agents (a), (b) and (c) is about 4:1 to about 20:1.

Separation step (2) can be carried out in any suitable manner. Preferably, the finished reaction mixture of step (1) is filtered, and the solid filter cake is substantially dried at any suitable conditions, preferably at subatmospheric (i.e., vacuum) conditions, at a temperature of about 25°–60° C. Preferably, step (2) is carried out under a dry inert gas atmosphere ($N_2$, He, Ar, and the like). Preferably, this catalyst preparation method consists essentially of steps (1) and (2). The finished/dried catalyst particles should be stored under a dry inert gas atmosphere.

In the second method for preparing catalysts employed in the alkylation process of the invention, step (A) is carried out substantially in the same manner as step (1) of the first method, except that ingredients (ii) and (iii) are used in lieu of ingredients (b) and (c). The molar ratio of agent (ii), i.e., aluminum phosphate, to agent (i), i.e., aluminum chloride, generally is in the range of about 0.05:1 to about 1:1, preferably about 0.1:1 to about 0.6:1. Generally, the ratio of the combined weights of agents (i) and (ii) to the weight of agent (iii), i.e., silica (having a $BET/N_2$ surface area of at least about 50 $m^2/g$, preferably about 100–400 $m^2/g$), is in the range of about 0.5:1 to about 5:1, preferably about 1:1 to about 2:1.

Agent (iv) is identical with agent (d) in the first preparation method. Non-limiting examples of effective chlorinated hydrocarbons which can be used as agent (iv) are listed above. The preferred agent (iv) is $CCl_4$. Generally, the ratio of the weight of agent (iv) to the combined weight of agents (i), (ii) and (iii) is about 4:1 to about 20:1.

It is preferably preferred to employ a mixture consisting essentially of agents (i), (ii), (iii) and (iv) in step (A). However, it is within the scope of this invention to also have at least one metal sulfate selected from the group consisting of copper(II) sulfate, iron(II) sulfate, cobalt(II) sulfate, nickel(II) sulfate, magnesium sulfate and calcium sulfate present in step (A), generally at a molar ratio of $AlCl_3$ to said at least one metal sulfate of about 2:1 to about 10:1.

Step (B) in the second catalyst preparation method is carried out in essentially the same manner as step (2), described above. In a presently preferred embodiment, this second catalyst preparation method consists essentially of steps (A) and (B). The finished/dried catalyst particles should be stored under a dry inert gas atmosphere.

The catalysts prepared by either the first or the second preparation method are employed in the alkylation process of this invention. The process for alkylating $C_3$–$C_6$ alkanes (preferably isoalkanes, i.e., branched alkanes) with $C_3$–$C_6$ alkenes (preferably those containing internal double bonds) can be carried out in any suitable manner. The contacting of a mixture of at least one feed alkane and at least one feed alkene, generally at a molar alkane/alkene ratio of about 1:1 to about 100:1 (preferably about 5:1 to about 15:1) with one of the above-described catalyst compositions can be carried out under any suitable reaction conditions at a relatively low temperature of up to about 100° C., more preferably about 20°–50° C., most preferably about 30°–40° C., generally at about 1–5 atm pressure. The alkane/alkene feed mixture can be contacted with the catalyst composition in any suitable mode, such as in a slurry-type operation in which the catalyst is dispersed in the alkane/alkene feed mixture, or in a fixed catalyst bed operation in which the feed mixture flows upward or downward through a solid catalyst layer (or several catalyst layers).

Suitable feed alkanes are normal (straight chain) alkanes and isoalkanes (i.e., branched) alkanes, each containing 3–6 carbon atoms per molecule. Non-limiting examples of suitable alkanes are n-butane, isobutane, n-pentane, isopentane (i.e., 2-methylbutane), n-hexane, and isohexanes (such as 2-methylpentane, 3-methylpentane, 2,2-dimethylbutane), trimethyl-substituted heptanes, tetramethyl-substituted hexanes). Presently preferred are $C_3$–$C_6$ isoalkanes (branched alkanes). Particularly preferred feed alkanes are isobutane and isopentane (2-methylbutane).

Suitable feed alkenes are normal (straight chain) and branched alkenes containing one C=C double bond, preferably an internal double bond (more preferably in the 2 position). Non-limiting examples of suitable alkenes are propylene, butene-1, butene-2, isobutylene, pentene-1, pentene-2, isopentenes, hexene-1, hexene-2, hexene-3 and isohexenes. The presently more preferred feed alkene is butene-2.

The alkylation process of this invention generally generates a multitude of hydrocarbon products, as is demonstrated in the examples. Thus, it is generally necessary to separate the various formed hydrocarbon products from one another and from unconverted feed hydrocarbons. This separation can be carried out in any suitable manner, generally by fractional distillation (possibly in the presence of an extractant, i.e., by extractive distillation), as can be determined by persons skilled in the various liquid-liquid separation technologies.

The following examples are provided to further illustrate the processes of this invention, and are not to be construed as unduly limiting the scope of this invention.

EXAMPLE I

This example illustrates the preparation of alkylation catalyst compositions in accordance with the first preparation method (described above).

A mixture of about 20 millimoles of dry $AlCl_3$, about 4.8 millimoles of an anhydrous metal sulfate ($CuSO_4$ or $NiSO_4$ or $CoSO_4$ or $FeSO_4$ or $MnSO_4$ or $ZnSO_4$ or $MgSO_4$ or $CaSO_4$), about 5.0 grams of an inorganic support material (described below), and about 60 mL of dried carbon tetrachloride was heated for about one day under reflux conditions in a dry nitrogen gas atmosphere. Thereafter, the slurry was cooled and filtered, and the solid catalyst material was dried for several hours under vacuum conditions. Control catalysts were prepared in accordance with the above procedure except that metal sulfates were absent.

The following support materials were employed in the above-described preparation: gamma-alumina (100 mesh trilobal extrudate; marketed by American Cyanamid Company, Deerfield, Ill.; BET/$N_2$ surface area: about 144 $m^2/g$; calcined in air for 2-3 hours at 700° C.); silica (calcined at 600° C. for 3 hours; BET/$N_2$ surface area: about 340 $m^2/g$; marketed by the Davison Catalyst Division of W. R. Grace and Company, Baltimore, Md., under the product designation of G-57); two silica-aluminas containing 50 weight-% silica and 50 weight-% alumina, and 25 weight-% silica and 75 weight-% alumina, respectively (both having been prepared by coprecipitating hydrated silica and hydrated alumina, followed by calcining at about 600° C. for about 2 hours; surface areas about 300-350 $m^2/g$); and an aluminum phosphate/oxide having an atomic P:Al ratio of 0.5:1, having been prepared by adding enough of a concentrated aqueous ammonia solution to an aqueous solution of $Al(NO_3)_3$ and $NH_4H_2PO_4$ to make the latter solution basic and to coprecipitate aluminum phosphate/hydroxide, followed by aging the coprecipitate under the basic solution for 1-2 hours, filtering the slurry, drying and calcining the filter cake in air for about 3 hours at 600° C.

EXAMPLE II

This example illustrates the use of the catalyst materials described in Example I for the alkylation of isobutane with butene-2.

About 5-8 grams of a feed mixture containing isobutane and butene-2 (molar ratio of isobutane to butene-2: about 10:1) and about 0.5 grams of one of the catalysts described in Example I were placed in a sealed glass flask. The feed/catalyst mixture was maintained at a temperature of about 30°-40° C. and a pressure of about 20 psig and was agitated with an ultrasound vibrator. After about 1 hour, the flask content was analyzed by means of a gas chromatograph. Test results are summarized in Table I, and demonstrate the superiority (in terms of butene-2 conversion) of the catalysts prepared from $AlCl_3$, various metal sulfates and various inorganic support materials versus control catalysts prepared without the metal sulfates.

TABLE I

| Catalyst Preparation Method | % Conversion of Butene-2 | Liquid Product Composition (Weight-%) | | | | Octane Number[4] |
|---|---|---|---|---|---|---|
| | | $C_3/C_4$ Alkanes | $C_5$-$C_7$ Alkanes | $C_2$ Alkanes | $C_9^+$ Alkanes | |
| $AlCl_3$ + $Al_2O_3$ (Control) | 79 | 6.4 | 9.6 | 25.3 | 58.7 | 90.0 |
| $AlCl_3$ + $SiO_2$ (Control) | 89 | 8.6 | 10.2 | 26.5 | 54.7 | 80.7 |
| $AlCl_3$ + $SiO_2/Al_2O_3$[2] (Control) | 92 | 9.7 | 11.3 | 32.4 | 46.7 | 81.7 |
| $AlCl_3$ + $CuSO_4$ + $Al_2O_3$ | 100 | 6.7 | 39.0 | 37.1 | 17.3 | 84.4 |
| $AlCl_3$ + $CuSO_4$ + $Al_2O_3$ | 99 | 24.3 | 47.2 | 21.4 | 7.1 | 84.2 |
| $AlCl_3$ + $CuSO_4$ + $Al_2O_3$ | 100 | 22.2 | 32.9 | 25.0 | 19.9 | 88.1 |
| $AlCl_3$ + $CuSO_4$ + $Al_2O_3$ | 100 | 3.4 | 40.2 | 32.7 | 23.8 | 84.3 |
| $AlCl_3$ + $CuSO_4$ + $Al_2O_3$ | 100 | 8.7 | 21.2 | 33.9 | 36.1 | 88.6 |
| $AlCl_3$ + $CuSO_4$ + $SiO_2$ | 100 | 3.9 | 21.4 | 53.1 | 21.6 | 87.8 |
| $AlCl_3$ + $CuSO_4$ + $SiO_2/Al_2O_3$[2] | 100 | 21.2 | 41.6 | 27.4 | 9.8 | 83.6 |
| $AlCl_3$ + $CuSO_4$ + $SiO_2/Al_2O_3$[2] | 94 | 0.8 | 16.4 | 43.8 | 38.1 | 88.2 |
| $AlCl_3$ + $CuSO_4$ + $SiO_2/Al_2O_3$[2] | 100 | 0.7 | 33.9 | 32.2 | 33.3 | 88.8 |
| $AlCl_3$ + $CuSO_4$ + $SiO_2/Al_2O_3$[2] | 100 | 35.4 | 22.9 | 29.7 | 12.0 | 92.6 |
| $AlCl_3$ + $CuSO_4$ + Al—$PO_4$ | 100 | 0.8 | 27.6 | 46.8 | 24.8 | 77.9 |
| $AlCl_3$ + $NiSO_4$ + $Al_2O_3$ | 100 | 58.6 | 9.8 | 18.8 | 12.2 | 88.7 |
| $AlCl_3$ + $NiSO_4$ + $Al_2O_3$ | 100 | 64.6 | 9.0 | 19.2 | 6.3 | 90.2 |
| $AlCl_3$ + $NiSO_4$ + $Al_2O_3$ | 100 | 30.2 | 19.6 | 27.5 | 22.8 | 90.6 |
| $AlCl_3$ + $NiSO_4$ + $Al_2O_3$ | 100 | 13.4 | 21.5 | 29.8 | 35.3 | 88.8 |
| $AlCl_3$ + $NiSO_4$ + $SiO_2$ | 100 | 16.2 | 19.1 | 29.0 | 32.3 | 90.4 |
| $AlCl_3$ + $NiSO_4$ + $SiO_2/Al_2O_3$[1] | 93* | 15.1* | 27.3* | 33.7* | 23.9* | 69.7* |
| $AlCl_3$ + $NiSO_4$ + $SiO_2/Al_2O_3$[2] | 100 | 43.0 | 15.8 | 29.5 | 11.8 | 83.6 |
| $AlCl_3$ + $NiSO_4$ + $SiO_2/Al_2O_3$[2] | 100 | 18.8 | 3.9 | 27.7 | 49.4 | 85.8 |
| $AlCl_3$ + $NiSO_4$ + Al—$PO_4$[3] | 100 | 4.1 | 3.2 | 30.0 | 60.9 | 83.6 |
| $AlCl_3$ + $CoSO_4$ + $Al_2O_3$ | 100 | 37.3 | 15.5 | 29.9 | 17.2 | 91.2 |
| $AlCl_3$ + $CoSO_4$ + $Al_2O_3$ | 99 | 53.8 | 4.4 | 17.1 | 24.8 | 88.1 |
| $AlCl_3$ + $CoSO_4$ + $Al_2O_3$ | 100 | 42.6 | 25.2 | 20.7 | 11.5 | 91.4 |
| $AlCl_3$ + $CoSO_4$ + $Al_2O_3$ | 100 | 29.3 | 5.7 | 17.8 | 41.2 | 83.7 |
| $AlCl_3$ + $CoSO_4$ + $SiO_2$ | 100 | 40.0 | 19.5 | 25.3 | 13.9 | 91.7 |
| $AlCl_3$ + $CoSO_4$ + $SiO_2/Al_2O_3$[1] | 100 | 35.6 | 34.8 | 16.8 | 12.8 | 71.4 |
| $AlCl_3$ + $CoSO_4$ + $SiO_2/Al_2O_3$[2] | 98 | 32.0 | 8.7 | 22.9 | 36.3 | 87.0 |
| $AlCl_3$ + $CoSO_4$ + $SiO_2/Al_2O_3$[2] | 100 | 7.3 | 7.0 | 39.7 | 45.9 | 85.1 |
| $AlCl_3$ + $CoSO_4$ + Al—$PO_4$[3] | 100 | 5.8 | 9.7 | 30.1 | 54.4 | 84.4 |
| $AlCl_3$ + $FeSO_4$ + $Al_2O_3$ | 100 | 45.3 | 22.2 | 20.6 | 11.8 | 85.6 |
| $AlCl_3$ + $FeSO_4$ + $Al_2O_3$ | 100 | 37.7 | 12.7 | 25.9 | 23.7 | 91.5 |
| $AlCl_3$ + $FeSO_4$ + $Al_2O_3$ | 100 | 28.4 | 21.9 | 26.3 | 23.4 | 90.1 |
| $AlCl_3$ + $FeSO_4$ + $Al_2O_3$ | 100 | 6.2 | 30.9 | 27.1 | 35.8 | 89.4 |
| $AlCl_3$ + $FeSO_4$ + $Al_2O_3$ | 100 | 10.5 | 10.3 | 30.3 | 48.8 | 87.7 |
| $AlCl_3$ + $FeSO_4$ + $SiO_2$ | 100 | 32.1 | 10.4 | 37.8 | 18.5 | 91.3 |
| $AlCl_3$ + $FeSO_4$ + $SiO_2/Al_2O_3$[1] | 100 | 46.9 | 19.8 | 22.3 | 10.9 | 87.5 |
| $AlCl_3$ + $FeSO_4$ + $SiO_2/Al_2O_3$[2] | 98 | 43.0 | 17.1 | 19.5 | 20.3 | 90.7 |
| $AlCl_3$ + $FeSO_4$ + $SiO_2/Al_2O_3$[2] | 100 | 40.5 | 28.5 | 18.7 | 12.2 | 92.1 |
| $AlCl_3$ + $FeSO_4$ + $SiO_2/Al_2O_3$[2] | 100 | 40.7 | 17.7 | 25.5 | 16.0 | 91.1 |
| $AlCl_3$ + $FeSO_4$ + Al—$PO_4$[3] | 100 | 2.8 | 8.9 | 38.8 | 48.8 | 86.6 |
| $AlCl_3$ + $MnSO_4$ + $Al_2O_3$ | 100 | 21.9 | 6.0 | 33.7 | 38.5 | 87.1 |
| $AlCl_3$ + $MnSO_4$ + $Al_2O_3$ | 100 | 50.3 | 7.4 | 34.7 | 7.6 | 93.4 |
| $AlCl_3$ + $MnSO_4$ + $Al_2O_3$ | 99 | 16.4 | 10.2 | 34.8 | 38.1 | 87.3 |
| $AlCl_3$ + $MnSO_4$ + $Al_2O_3$ | 99 | 51.7 | 14.5 | 20.4 | 13.4 | 88.5 |
| $AlCl_3$ + $MnSO_4$ + $SiO_2$ | 99 | 47.1 | 5.8 | 8.4 | 37.5 | 83.7 |
| $AlCl_3$ + $MnSO_4$ + $SiO_2/Al_2O_3$[1] | 100 | 15.7 | 24.8 | 36.0 | 25.5 | 75.8 |

TABLE I-continued

| Catalyst Preparation Method | % Conversion of Butene-2 | Liquid Product Composition (Weight-%) | | | | Octane Number[4] |
|---|---|---|---|---|---|---|
| | | $C_3/C_4$ Alkanes | $C_5$-$C_7$ Alkanes | $C_2$ Alkanes | $C_9^+$ Alkanes | |
| $AlCl_3$ + $MnSO_4$ + $SiO_2/Al_2O_3$[2] | 100 | 35.4 | 16.4 | 21.9 | 26.3 | 89.2 |
| $AlCl_3$ + $MnSO_4$ + $SiO_2/Al_2O_3$[2] | 98 | 1.8 | 19.6 | 29.2 | 49.2 | 77.6 |
| $AlCl_3$ + $MnSO_4$ + Al—$PO_4$ | 100 | 22.6 | 13.6 | 33.4 | 30.2 | 88.3 |
| $AlCl_3$ + $ZnSO_4$ + $Al_2O_3$ | 100 | 35.3 | 14.1 | 25.4 | 25.1 | 87.9 |
| $AlCl_3$ + $ZnSO_4$ + $Al_2O_3$ | 100 | 1.7 | 9.9 | 42.7 | 45.7 | 87.9 |
| $AlCl_3$ + $ZnSO_4$ + $Al_2O_3$ | 100 | 36.9 | 20.2 | 22.5 | 20.5 | 91.1 |
| $AlCl_3$ + $ZnSO_4$ + $SiO_2$ | 100 | 20.8 | 33.7 | 28.6 | 16.5 | 89.3 |
| $AlCl_3$ + $ZnSO_4$ + $SiO_2/Al_2O_3$[1] | 100 | 8.0 | 26.2 | 34.4 | 31.4 | 84.7 |
| $AlCl_3$ + $ZnSO_4$ + $SiO_2/Al_2O_3$[2] | 98 | 33.7 | 16.6 | 22.7 | 26.9 | 90.7 |
| $AlCl_3$ + $ZnSO_4$ + $SiO_2/Al_2O_3$[2] | 100 | 0.7 | 4.3 | 29.7 | 65.2 | 84.4 |
| $AlCl_3$ + $ZnSO_4$ + $SiO_2$/Al—$PO_4$[3] | 100 | 5.2 | 11.3 | 35.6 | 46.7 | 87.0 |
| $AlCl_3$ + $MgSO_4$ + $Al_2O_3$ | 100 | 32.8 | 27.4 | 13.9 | 21.4 | 74.0 |
| $AlCl_3$ + $MgSO_4$ + $Al_2O_3$ | 100 | 11.2 | 21.7 | 34.9 | 32.2 | 89.1 |
| $AlCl_3$ + $MgSO_4$ + $Al_2O_3$ | 99 | 1.7 | 9.6 | 35.8 | 52.9 | 86.6 |
| $AlCl_3$ + $MgSO_4$ + $Al_2O_3$ | 96 | 14.6 | 18.1 | 39.0 | 28.3 | 89.0 |
| $AlCl_3$ + $MgSO_4$ + $SiO_2$ | 100 | 41.7 | 18.7 | 22.6 | 16.4 | 91.3 |
| $AlCl_3$ + $MgSO_4$ + $SiO_2/Al_2O_3$[1] | 99 | 34.7 | 15.7 | 29.1 | 23.5 | 75.8 |
| $AlCl_3$ + $MgSO_4$ + $SiO_2/Al_2O_3$[2] | 98 | 1.9 | 11.1 | 35.5 | 51.6 | 87.9 |
| $AlCl_3$ + $MgSO_4$ + $SiO_2/Al_2O_3$[2] | 97 | 2.6 | 13.6 | 36.3 | 47.6 | 86.2 |
| $AlCl_3$ + $MgSO_4$ + Al—$PO_4$[3] | 100 | 5.9 | 8.0 | 38.7 | 46.2 | 87.2 |
| $AlCl_3$ + $CaSO_4$ + $Al_2O_3$ | 100 | 37.5 | 34.4 | 15.9 | 12.1 | 89.6 |
| $AlCl_3$ + $CaSO_4$ + $Al_2O_3$ | 99 | 1.0 | 20.5 | 37.1 | 41.4 | 90.3 |
| $AlCl_3$ + $CaSO_4$ + $Al_2O_3$ | 100 | 11.8 | 11.7 | 28.6 | 47.7 | 87.1 |
| $AlCl_3$ + $CaSO_4$ + $Al_2O_3$ | 100 | 53.1 | 17.9 | 21.6 | 7.4 | 87.1 |
| $AlCl_3$ + $CaSO_4$ + $SiO_2$ | 100 | 12.3 | 22.8 | 34.8 | 29.9 | 88.5 |
| $AlCl_3$ + $CaSO_4$ + $SiO_2/Al_2O_3$[1] | 100 | 22.1 | 37.8 | 23.9 | 16.3 | 79.2 |
| $AlCl_3$ + $CaSO_4$ + $SiO_2/Al_2O_3$[2] | 100 | 10.6 | 22.3 | 30.6 | 36.5 | 90.5 |
| $AlCl_3$ + $CaSO_4$ + $SiO_2/Al_2O_3$[2] | 100 | 50.1 | 23.3 | 15.4 | 11.2 | 91.5 |
| $AlCl_3$ + $CaSO_4$ + $SiO_2$/Al—$PO_4$[3] | 100 | 10.1 | 7.3 | 36.6 | 46.0 | 86.3 |

[1] 50 weight-% silica + 50 weight-% $Al_2O_3$
[2] 25 weight-% silica + 75 weight-% $Al_2O_3$
[3] aluminum phosphate/oxide having a P:Al atomic ratio of 0.5:1
[4] (research octane number + motor octane number) divide by 2
*test data believed to be erroneous

EXAMPLE III

This example illustrates the preparation and performance of additional alkylation catalyst materials, prepared by the second, above-described preparation method.

A mixture of about 2.5 grams of calcined silica (described in Example I), 1.78 grams (13.34 millimoles) of dry $AlCl_3$, various amounts of aluminum phosphate ($AlPO_4$; provided by Aldrich Chemical Company, Milwaukee, Wis.) and 35 mL to dried carbon tetrachloride was heated for 18 hours under reflux conditions in a dry nitrogen atmosphere. The amounts of aluminum phosphate employed in four separate catalyst preparations were 0.16 grams, 0.25 grams, 047 grams and 0.95 grams, respectively, so as to provide molar ratios of $AlPO_4$:$AlCl_3$ in the total mixture of about 0.15:1, 0.20:1, 0.29:1 and 0.58:1 respectively. Thereafter, the slurry was cooled and filtered, and the solid catalyst material was dried for several hours under vacuum conditions. A control catalyst was prepared according to the above procedure, but without added $AlPO_4$.

The above-described materials were tested as catalyst in the alkylation of isobutane and butene-2, essentially in accordance with the procedure described in Example II, except that the hydrocarbon feed mixture contained about 90 weight-% isobutane and about 10 weight-% butene-2. Test results, obtained after a reaction time of about 0.5 hour, are summarized in Table II.

TABLE II

| Catalyst Preparation Method | % Conversion of Butene-2 | Liquid Product Composition (Weight-%) | | | | Octane Number[5] |
|---|---|---|---|---|---|---|
| | | $C_4$ Alkanes | $C_5$-$C_7$ Alkanes | $C_8$ Alkanes | $C_9^+$ Alkanes | |
| $AlCl_3$ + $SiO_2$ (Control) | 96 | 11.9 | 14.3 | 29.1 | 44.8 | 82.2 |
| $AlCl_3$ + $SiO_2$ (Control) | 96 | 12.2 | 15.1 | 30.3 | 42.4 | 81.9 |
| $AlCl_3$ + $SiO_2$ (Control) | 96 | 12.1 | 14.6 | 29.8 | 43.5 | 82.7 |
| $AlCl_3$ + $SiO_2$ + $AlPO_4$[1] | 100 | 10.5 | 18.9 | 30.4 | 40.2 | 84.3 |
| $AlCl_3$ + $SiO_2$ + $AlPO_4$[2] | 100 | 11.1 | 20.2 | 33.1 | 35.6 | 84.9 |
| $AlCl_3$ + $SiO_2$ + $AlPO_4$[3] | 100 | 12.8 | 20.6 | 30.5 | 36.1 | 84.0 |
| $AlCl_3$ + $SiO_2$ + $AlPO_4$[4] | 100 | 12.2 | 21.4 | 31.6 | 34.8 | 84.3 |

[1] molar ratio of $AlPO_4$ to $AlCl_3$: 0.15:1
[2] molar ratio of $AlPO_4$ to $AlCl_3$: 0.20:1
[3] molar ratio of $AlPO_4$ to $AlCl_3$: 0.29:1
[4] molar ratio of $AlPO_4$ to $AlCl_3$: 0.58:1
[5] (research octane number + motor octane number) divided by 2

Test data in Table II clearly show that the catalyst materials prepared from $AlCl_3$, $AlPO_4$ and $SiO_2$ were more active as alkylation catalysts and also produced alkylates having higher octane numbers than the control catalyst material prepared from $AlCl_3$ and $SiO_2$ (without $AlPO_4$). Based on these test results and those presented in Table I, it is concluded that materials prepared from $AlCl_3$, $AlPO_4$, $SiO_2$ and at least one of the metal sulfates listed on page 2 would be even more effective alkylation catalysts than those prepared from $AlCl_3$, $AlPO_4$ and $SiO_2$ (described above).

Reasonable variations, modifications and adaptations for various conditions can be made within the scope of the disclosure and the appended claims without departing from the scope of this invention.

That which is claimed is:

1. A process for alkylating alkanes which consist essentially of contacting at least one feed alkane containing about 3-6 carbon atoms per molecule with at least one alkene containing about 3-6 carbon atoms per molecule with at least one solid catalyst composition at effective alkylation conditions, so as to form an alkylate comprising at least one product alkane which contains a greater number of carbon atoms per molecule than said at least one feed alkane; wherein said solid catalyst composition has been prepared by a preparation method consisting essentially of the steps of:
   (1) heating for a period of at least 1 hour, at a temperature in the range of about 40° C. to about 90° C., in the substantial absence of water, a mixture consisting essentially of: (a) aluminum chloride, (b) at least one metal sulfate selected from the group consisting of copper(II) sulfate, nickel(II) sulfate, cobalt(II) sulfate, iron(II) sulfate, magnesium sulfate and calcium sulfate, (c) at least one solid inorganic refractory material having a surface area, measured by the BET method employing $N_2$, of at least about 50 m$^2$/g, selected from the group consisting of alumina, silica, silica-alumina, aluminum phosphate and aluminum phosphate/oxide, and (d) at least one chlorinated hydrocarbon selected from the group consisting of dichloromethane, chloroform, carbon tetrachloride, 1,1-dichloroethane, 1,2-dichloroethane, 1,1,1-trichloroethane, 1,1-dichloropropane, 2,2-dichloropropane, 1-chlorobutane and 2-chloro-2-methylbutane; wherein the molar ratio of aluminum chloride to said at least one metal sulfate is at least about 2:1; and
   (2) separating the solid component of the reaction mixture formed in step (1) from said at least one chlorinated hydrocarbon under a dry gas atmosphere.

2. A process in accordance with claim 1, wherein said at least one chlorinated hydrocarbon is carbon tetrachloride.

3. A process in accordance with claim 1, wherein said molar ratio of aluminum chloride to said at least one metal sulfate is about 5:1 to about 6:1, said surface area of said at least one solid inorganic refractory material is about 100-400 m$^2$/g, step (1) is carried out under an inert gas atmosphere, and the heating time in step (1) is about 5-30 hours.

4. A process in accordance with claim 1, wherein step (2) is carried out under an inert gas atmosphere in two sub-steps: filtering the reaction mixture formed in step (1) so as to recover said solid component therefrom, and then drying the recovered solid material.

5. A process in accordance with claim 1, wherein the ratio of the combined weights of agents (a) and (b) to the weight of agent (c) is about 0.5:1 to about 5:1.

6. A process in accordance with claim 5, wherein the ratio of the weight of agent (d) to the combined weights of agents (a), (b) and (c) is about 4:1 to about 20:1.

7. A process in accordance with claim 1, wherein said alkylation conditions comprise a molar alkane/alkene ratio of about 1:1 to about 100:1 and a reaction temperature of up to about 100° C., and wherein said at least one product alkane contains 3-6 more carbon atoms per molecule than said at least one feed alkane.

8. A process in accordance with claim 7, wherein said molar alkane/alkene ratio is about 5:1 to about 15:1 and said reaction temperature is about 20°-50° C.

9. A process in accordance with claim 1, wherein said at least one feed alkane is at least one branched alkane and said at least one alkene contains an internal double bond.

10. A process in accordance with claim 9, wherein said at least one branched alkane is selected from the group consisting of isobutane and isopentane, and said at least one alkene is butene-2.

11. A process for alkylating alkanes which consist essentially of contacting at least one feed alkane containing about 3-6 carbon atoms per molecule with at least one alkene containing about 3-6 carbon atoms per molecule with at least one solid catalyst composition at effective alkylation conditions, so as to form an alkylate comprising at least one product alkane which contains a greater number of carbon atoms per molecule than said at least one feed alkane; wherein said solid catalyst composition has been prepared by a preparation method consisting essentially of the steps of:
   (A) heating for a period of at least 1 hour, at a temperature in the range of about 40° C. to about 90° C., in the substantial absence of water, a mixture consisting essentially of: (i) aluminum chloride, (ii) aluminum phosphate, (iii) silica having a surface area, measured by the BET method employing $N_2$, of at least about 50 m$^2$/g, and (iv) at least one chlorinated hydrocarbon dichloromethane, chloroform, carbon tetrachloride, 1,1-dichloroethane, 1,2-dichloroethane, 1,1,1-trichloroethane, 1,1-dichloropropane, 2,2-dichloropropane, 1-chlorobutane and 2-chloro-2-methylbutane; and
   (B) separating the solid component of the reaction mixture formed in step (A) from said at least one chlorinated hydrocarbon under a dry gas atmosphere.

12. A process in accordance with claim 11, wherein said at least one chlorinated hydrocarbon is carbon tetrachloride.

13. A process in accordance with claim 11, wherein the molar ratio of aluminum phosphate to aluminum chloride is about 0.05:1 to about 1:1, step (A) is carried out under an inert gas atmosphere, and the heating time of step (A) is about 5-30 hours.

14. A process in accordance with claim 11, wherein step (B) is carried out under an inert gas atmosphere in two sub-steps: filtering the reaction mixture formed in step (A) so as to recover said solid component therefrom, and then drying the recovered solid material.

15. A process in accordance with claim 11, wherein said surface area of silica is about 100-400 m$^2$/g, and the molar ratio of aluminum phosphate to aluminum chloride in step (A) is about 0.1:1 to about 0.6:1.

16. A process in accordance with claim 15, wherein the ratio of the combined weights of agents (i) and (ii) to the weight of agent (iii) is about 0.5:1 to about 5:1, and the weight of agent (iv) to the combined weights of agents (i), (ii) and (iii) is about 4:1 to about 20:1.

17. A process in accordance with claim 11, wherein said alkylation conditions comprise a molar alkane/alkene ratio of about 1:1 to about 100:1 and a reaction temperature of up to about 100° C., and wherein said at least one product alkane contains 3-6 more carbon atoms per molecule than said at least one feed alkane.

18. A process in accordance with claim 17, wherein said molar alkane/alkene ratio is about 5:1 to about 15:1, and said reaction temperature is about 20°-50° C.

19. A process in accordance with claim 11, wherein said at least one feed alkane is at least one branched alkane, and said at least one alkene contains an internal double bond.

20. A process in accordance with claim 19, wherein said at least one branched alkane is selected from the group consisting of isobutane and isopentane, and said at least one alkene is butene-2.

* * * * *